(12) United States Patent
Chao

(10) Patent No.: US 8,361,129 B2
(45) Date of Patent: Jan. 29, 2013

(54) LARGE DIAMETER BONE ANCHOR ASSEMBLY

(75) Inventor: Nam Chao, Marlborough, MA (US)

(73) Assignee: DePuy Spine, Inc., Raynham, MA (US)

( * ) Notice: Subject to any disclaimer, the term of this patent is extended or adjusted under 35 U.S.C. 154(b) by 651 days.

(21) Appl. No.: 11/741,172

(22) Filed: Apr. 27, 2007

(65) Prior Publication Data

US 2008/0015580 A1 Jan. 17, 2008

Related U.S. Application Data

(60) Provisional application No. 60/796,019, filed on Apr. 28, 2006.

(51) Int. Cl.
*A61B 17/04* (2006.01)
*A61B 17/86* (2006.01)
*A61F 2/08* (2006.01)

(52) U.S. Cl. .................. 606/305; 606/264; 606/300

(58) Field of Classification Search .............. 606/246, 606/264–278, 300–321
See application file for complete search history.

(56) References Cited

U.S. PATENT DOCUMENTS

| | | |
|---|---|---|
| 5,034,011 A | 7/1991 | Howland |
| 5,098,434 A | 3/1992 | Serbousek |
| 5,102,412 A | 4/1992 | Rogozinski |
| 5,108,399 A | 4/1992 | Eitenmuller |
| 5,147,360 A | 9/1992 | Dubousset |
| 5,180,393 A | 1/1993 | Commarmond |
| 5,181,917 A | 1/1993 | Rogozinski |
| 5,217,497 A | 6/1993 | Mehdian |
| 5,242,443 A | 9/1993 | Kambin |
| 5,261,907 A | 11/1993 | Vignaud |
| 5,360,448 A | 11/1994 | Thramann |
| 5,368,594 A | 11/1994 | Martin |
| 5,375,823 A | 12/1994 | Navas |
| 5,443,467 A | 8/1995 | Biedermann |
| 5,480,438 A | 1/1996 | Arima |
| 5,498,263 A | 3/1996 | DiNello |
| 5,501,684 A | 3/1996 | Schlapfer |
| 5,505,736 A | 4/1996 | Reimels |
| 5,520,689 A | 5/1996 | Schlapfer |
| 5,549,677 A | 8/1996 | Durr |
| 5,562,663 A | 10/1996 | Wisnewski |
| 5,571,102 A | 11/1996 | Cavagna |
| 5,584,831 A | 12/1996 | McKay |
| 5,589,684 A | 12/1996 | Ventrudo |
| 5,591,166 A | 1/1997 | Bernhardt |

(Continued)

FOREIGN PATENT DOCUMENTS

| | | |
|---|---|---|
| CN | 201085681 | 7/2008 |
| EP | 289192 | 1/1992 |

(Continued)

OTHER PUBLICATIONS

Harms, "Posterior C1-C2 Fusion With Polyaxial Screw and Rod Fixation"; Spine; Nov. 15, 2001; pp. 2467-2471; vol. 26(22); Lippincott Williams & Wilkins.

(Continued)

*Primary Examiner* — Eduardo C Robert
*Assistant Examiner* — Christina Negrellirodriguez

(57) ABSTRACT

A bone anchor assembly is described having a large diameter for fixing a spinal connection element to bone. The assembly includes a receiver member for receiving the spinal connection element, a bone-engaging shank for engaging bone and a first and second insert for retaining the head of the shank within the receiver member.

11 Claims, 6 Drawing Sheets

U.S. PATENT DOCUMENTS

| | | | |
|---|---|---|---|
| 5,630,817 A | 5/1997 | Rokegem | |
| 5,643,260 A | 7/1997 | Doherty | |
| 5,647,873 A | 7/1997 | Errico | |
| 5,669,911 A | 9/1997 | Errico | |
| 5,672,176 A | 9/1997 | Biedermann | |
| 5,683,390 A | 11/1997 | Metz-Stavenhagen | |
| 5,688,274 A | 11/1997 | Errico | |
| 5,690,630 A | 11/1997 | Errico | |
| 5,725,528 A | 3/1998 | Errico | |
| 5,728,098 A | 3/1998 | Sherman | |
| 5,733,285 A | 3/1998 | Errico | |
| 5,735,851 A | 4/1998 | Errico | |
| 5,738,685 A | 4/1998 | Halm | |
| 5,782,833 A | 7/1998 | Haider | |
| 5,790,543 A | 8/1998 | Cloutier | |
| 5,797,911 A | 8/1998 | Sherman | |
| 5,810,819 A | 9/1998 | Errico | |
| 5,817,094 A | 10/1998 | Errico | |
| 5,863,293 A | 1/1999 | Richelsoph | |
| 5,879,350 A | 3/1999 | Sherman | |
| 5,882,350 A | 3/1999 | Ralph | |
| 5,885,286 A | 3/1999 | Sherman | |
| 5,891,145 A | 4/1999 | Morrison | |
| 5,902,303 A | 5/1999 | Eckhof | |
| 5,910,142 A | 6/1999 | Tatar | |
| 5,954,725 A | 9/1999 | Sherman | |
| 5,961,516 A | 10/1999 | Graf | |
| 5,964,760 A | 10/1999 | Richelsoph | |
| 5,997,539 A | 12/1999 | Errico | |
| 6,004,349 A | 12/1999 | Jackson | |
| 6,007,539 A | 12/1999 | Kirsch | |
| 6,010,503 A | 1/2000 | Richelsoph | |
| 6,022,350 A | 2/2000 | Ganem | |
| 6,050,997 A | 4/2000 | Mullane | |
| 6,053,917 A | 4/2000 | Sherman | |
| 6,063,090 A | 5/2000 | Schlapfer | |
| 6,077,262 A | 6/2000 | Schlapfer | |
| 6,083,226 A | 7/2000 | Fiz | |
| 6,090,110 A | 7/2000 | Metz Stavenhagen | |
| 6,113,601 A | 9/2000 | Tatar | |
| 6,132,432 A | 10/2000 | Richelsoph | |
| 6,132,434 A | 10/2000 | Sherman | |
| 6,139,549 A | 10/2000 | Keller | |
| 6,146,383 A | 11/2000 | Studer | |
| 6,183,472 B1 | 2/2001 | Lutz | |
| 6,214,006 B1 | 4/2001 | Metz Stavenhagen | |
| 6,224,598 B1 | 5/2001 | Jackson | |
| 6,248,105 B1 | 6/2001 | Schläpfer | |
| 6,251,112 B1 | 6/2001 | Jackson | |
| 6,254,602 B1 | 7/2001 | Justis | |
| 6,261,287 B1 | 7/2001 | Metz Stavenhagen | |
| 6,280,442 B1 | 8/2001 | Barker | |
| 6,287,311 B1 | 9/2001 | Sherman | |
| 6,302,888 B1 | 10/2001 | Mellinger | |
| 6,355,040 B1 | 3/2002 | Richelsoph | |
| 6,361,535 B2 | 3/2002 | Jackson | |
| RE37,665 E | 4/2002 | Ralph | |
| 6,371,957 B1 | 4/2002 | Amrein | |
| 6,379,356 B1 | 4/2002 | Jackson | |
| 6,402,752 B2 | 6/2002 | Schäffler-Wachter | |
| 6,440,132 B1 | 8/2002 | Jackson | |
| 6,454,773 B1 | 9/2002 | Sherman | |
| 6,471,705 B1 | 10/2002 | Biedermann | |
| 6,471,707 B1 | 10/2002 | Miller | |
| 6,482,207 B1 | 11/2002 | Errico | |
| 6,485,494 B1 | 11/2002 | Haider | |
| 6,488,681 B2 | 12/2002 | Martin | |
| 6,520,963 B1 | 2/2003 | McKinley | |
| 6,521,264 B1 | 2/2003 | Lacout | |
| 6,537,276 B2 | 3/2003 | Metz Stavenhagen | |
| 6,540,749 B2 | 4/2003 | Schäfer | |
| 6,547,792 B1 | 4/2003 | Tsuji | |
| 6,554,834 B1 | 4/2003 | Crozet | |
| 6,565,567 B1 | 5/2003 | Haider | |
| 6,565,569 B1 | 5/2003 | Assaker | |
| 6,569,164 B1 | 5/2003 | Assaker | |
| 6,582,436 B2 | 6/2003 | Schlapfer | |
| 6,626,908 B2 | 9/2003 | Cooper | |
| 6,641,583 B2 | 11/2003 | Shluzas | |
| 6,652,526 B1 | 11/2003 | Arafiles | |
| 6,660,004 B2 | 12/2003 | Barker | |
| 6,663,634 B2 | 12/2003 | Ahrens | |
| 6,672,788 B2 | 1/2004 | Hathaway | |
| 6,716,214 B1 | 4/2004 | Jackson | |
| 6,723,100 B2 * | 4/2004 | Biedermann et al. | 606/308 |
| 6,726,687 B2 | 4/2004 | Jackson | |
| 6,730,089 B2 | 5/2004 | Jackson | |
| 6,733,503 B2 | 5/2004 | Layrolle | |
| 6,749,612 B1 | 6/2004 | Conchy | |
| 6,755,829 B1 | 6/2004 | Bono | |
| 6,786,903 B2 | 9/2004 | Lin | |
| 6,835,196 B2 | 12/2004 | Biedermann | |
| 6,869,433 B2 | 3/2005 | Glascott | |
| 6,881,215 B2 | 4/2005 | Assaker | |
| 6,887,242 B2 | 5/2005 | Doubler | |
| 6,896,677 B1 | 5/2005 | Lin | |
| 6,905,500 B2 | 6/2005 | Jeon | |
| 6,916,321 B2 | 7/2005 | TenHuisen | |
| 6,918,911 B2 | 7/2005 | Biedermann | |
| 7,008,423 B2 | 3/2006 | Assaker | |
| 7,022,122 B2 | 4/2006 | Amrein | |
| RE39,089 E | 5/2006 | Ralph | |
| 7,063,702 B2 | 6/2006 | Michelson | |
| 7,090,674 B2 | 8/2006 | Doubler | |
| 7,156,850 B2 | 1/2007 | Kim | |
| 7,179,261 B2 | 2/2007 | Sicvol | |
| 7,186,255 B2 | 3/2007 | Baynham | |
| 7,204,838 B2 | 4/2007 | Jackson | |
| 7,211,086 B2 | 5/2007 | Biedermann | |
| 7,261,714 B2 | 8/2007 | Richelsoph | |
| 7,306,606 B2 | 12/2007 | Sasing | |
| 7,322,981 B2 | 1/2008 | Jackson | |
| 7,326,210 B2 | 2/2008 | Jahng | |
| 7,476,228 B2 | 1/2009 | Abdou | |
| 7,604,655 B2 | 10/2009 | Warnick | |
| 7,625,394 B2 | 12/2009 | Molz, IV | |
| 7,625,396 B2 * | 12/2009 | Jackson | 606/305 |
| 7,662,172 B2 | 2/2010 | Warnick | |
| 7,862,588 B2 | 1/2011 | Abdou | |
| 8,012,185 B2 | 9/2011 | Warnick | |
| 8,133,262 B2 * | 3/2012 | Whipple | 606/269 |
| 8,167,910 B2 * | 5/2012 | Nilsson | 606/264 |
| 2002/0151900 A1 | 10/2002 | Glascott | |
| 2002/0183748 A1 | 12/2002 | Martin | |
| 2003/0004512 A1 | 1/2003 | Farris | |
| 2003/0032957 A1 | 2/2003 | McKinley | |
| 2003/0109880 A1 | 6/2003 | Shirado | |
| 2003/0125741 A1 * | 7/2003 | Biedermann et al. | 606/61 |
| 2003/0149432 A1 | 8/2003 | Frigg | |
| 2004/0049189 A1 | 3/2004 | Le Couedic | |
| 2004/0049190 A1 | 3/2004 | Biedermann | |
| 2004/0097933 A1 * | 5/2004 | Lourdel et al. | 606/61 |
| 2004/0102781 A1 | 5/2004 | Jeon | |
| 2004/0106925 A1 | 6/2004 | Culbert | |
| 2004/0111088 A1 | 6/2004 | Picetti | |
| 2004/0127899 A1 | 7/2004 | Konieczynski | |
| 2004/0143264 A1 | 7/2004 | McAfee | |
| 2004/0143267 A1 | 7/2004 | Fallin | |
| 2004/0158247 A1 | 8/2004 | Sitiso | |
| 2004/0172022 A1 | 9/2004 | Landry | |
| 2004/0181224 A1 | 9/2004 | Biedermann | |
| 2004/0225289 A1 | 11/2004 | Biedermann | |
| 2004/0236327 A1 | 11/2004 | Paul | |
| 2004/0236328 A1 | 11/2004 | Paul | |
| 2004/0236330 A1 | 11/2004 | Purcell | |
| 2004/0267264 A1 * | 12/2004 | Konieczynski et al. | 606/73 |
| 2005/0027292 A1 | 2/2005 | Bernard | |
| 2005/0038438 A1 | 2/2005 | Anderson | |
| 2005/0049588 A1 | 3/2005 | Jackson | |
| 2005/0049589 A1 | 3/2005 | Jackson | |
| 2005/0055026 A1 | 3/2005 | Biedermann | |
| 2005/0065514 A1 | 3/2005 | Studer | |
| 2005/0080415 A1 | 4/2005 | Keyer | |
| 2005/0096654 A1 | 5/2005 | Lin | |
| 2005/0131408 A1 | 6/2005 | Sicvol | |
| 2005/0154391 A1 | 7/2005 | Doherty | |
| 2005/0165396 A1 | 7/2005 | Fortin | |

| | | |
|---|---|---|
| 2005/0171542 A1 | 8/2005 | Biedermann |
| 2005/0171543 A1 | 8/2005 | Timm |
| 2005/0177156 A1 | 8/2005 | Timm |
| 2005/0182401 A1 | 8/2005 | Timm |
| 2005/0187549 A1 | 8/2005 | Jackson |
| 2005/0203516 A1 | 9/2005 | Biedermann |
| 2005/0222569 A1 | 10/2005 | Panjabi |
| 2005/0245930 A1 | 11/2005 | Timm |
| 2005/0261685 A1 | 11/2005 | Fortin |
| 2005/0273101 A1 | 12/2005 | Schumacher |
| 2005/0277920 A1 | 12/2005 | Slivka |
| 2005/0277922 A1 | 12/2005 | Trieu |
| 2005/0277928 A1 | 12/2005 | Boschert |
| 2005/0288670 A1 | 12/2005 | Panjabi |
| 2006/0025767 A1 | 2/2006 | Khalili |
| 2006/0036252 A1 | 2/2006 | Baynham |
| 2006/0041259 A1 | 2/2006 | Paul |
| 2006/0084981 A1 | 4/2006 | Shluzas |
| 2006/0100621 A1 | 5/2006 | Jackson |
| 2006/0100622 A1 | 5/2006 | Jackson |
| 2006/0142772 A1 | 6/2006 | Ralph |
| 2006/0149231 A1 | 7/2006 | Bray |
| 2006/0149232 A1 | 7/2006 | Sasing |
| 2006/0149235 A1 | 7/2006 | Jackson |
| 2006/0149240 A1 | 7/2006 | Jackson |
| 2006/0149244 A1 | 7/2006 | Amrein |
| 2006/0161152 A1 | 7/2006 | Ensign |
| 2006/0190002 A1 | 8/2006 | Tallarida |
| 2006/0247631 A1 | 11/2006 | Ahn |
| 2006/0264937 A1 | 11/2006 | White |
| 2006/0276788 A1 | 12/2006 | Berry |
| 2006/0293659 A1 | 12/2006 | Alvarez |
| 2007/0049933 A1 | 3/2007 | Ahn |
| 2007/0055240 A1 | 3/2007 | Matthis |
| 2007/0055241 A1 | 3/2007 | Matthis |
| 2007/0118117 A1 | 5/2007 | Altarac |
| 2007/0161985 A1 | 7/2007 | Demakas |
| 2007/0191835 A1 | 8/2007 | Justis |
| 2007/0233078 A1 | 10/2007 | Justis |
| 2007/0270838 A1 | 11/2007 | Bruneau |
| 2008/0004625 A1 | 1/2008 | Runco |
| 2008/0015576 A1 | 1/2008 | Whipple |
| 2008/0015579 A1 | 1/2008 | Whipple |
| 2008/0015596 A1 | 1/2008 | Whipple |
| 2008/0015597 A1 | 1/2008 | Whipple |
| 2008/0033435 A1 | 2/2008 | Studer |
| 2008/0125816 A1 | 5/2008 | Jackson |
| 2008/0132957 A1 | 6/2008 | Matthis |
| 2008/0177323 A1 | 7/2008 | Null |
| 2008/0234761 A1 | 9/2008 | Jackson |
| 2008/0269809 A1 | 10/2008 | Garamszegi |
| 2008/0287998 A1 | 11/2008 | Doubler |
| 2008/0288003 A1 | 11/2008 | McKinley |
| 2008/0306554 A1 | 12/2008 | McKinley |
| 2009/0024174 A1 | 1/2009 | Stark |
| 2009/0036893 A1 | 2/2009 | Kartalian |
| 2009/0036934 A1 | 2/2009 | Biedermann |
| 2009/0087472 A1 | 4/2009 | Murphy |
| 2010/0057125 A1 | 3/2010 | Viker |
| 2011/0093021 A1 | 4/2011 | Fanger |

FOREIGN PATENT DOCUMENTS

| | | |
|---|---|---|
| EP | 465158 | 3/1992 |
| EP | 599766 | 6/1994 |
| EP | 532421 | 11/1995 |
| EP | 465158 | 1/1997 |
| EP | 767636 | 1/1999 |
| EP | 1747760 | 10/2009 |
| EP | 1776927 | 9/2010 |
| WO | WO 9322983 | 11/1993 |
| WO | WO 9407425 | 4/1994 |
| WO | WO 9501132 | 1/1995 |
| WO | WO 9513755 | 5/1995 |
| WO | WO 9531158 | 11/1995 |
| WO | WO 9702786 | 1/1997 |
| WO | WO 9902200 | 1/1999 |
| WO | WO 9938451 | 8/1999 |
| WO | WO 02069854 | 9/2002 |
| WO | WO 03041599 | 5/2003 |
| WO | WO 2004041100 | 5/2004 |
| WO | WO 2004064653 | 8/2004 |
| WO | WO 2005027761 | 3/2005 |
| WO | WO 2006116437 A3 | 2/2007 |
| WO | WO 2006115539 A3 | 5/2007 |
| WO | WO 2007075454 | 7/2007 |
| WO | WO 2007067857 A3 | 2/2008 |
| WO | WO 2008003047 | 6/2008 |

OTHER PUBLICATIONS

Stokes, "Posterior Atlantoaxial Stabilization New Alternative to C1-C2 Transarticular Screw"; Neurosurg Focus; Jan. 15, 2002; pp. 1-5; vol. 12(1); Article 6.

Mumaneni, "Posterior Cervical Fixation Using a New Polyaxial Screw and System: Technique and Surgical Results"; Neurosurg Focus; Jan. 15, 2002; pp. 1-5; vol. 12(1); Article 8.

Schultheiss, "MACS TL Polyaxialscrew XL a New Concept to Increase the Stability of Ventral Spondylodesis in the Presence of Dorsal Structure Injuries"; Orthopade; Apr. 2002; pp. 397-401; vol. 31(4); Springer-Verlag.

Fogel, "Physical Characteristics of Polyaxial-Headed Pedicle Screws and Biochemical Comparison of Load With Their Failure"; Spine; Mar. 1, 2003; pp. 397-401; vol. 28(5); Lippincott Williams & Wilkins.

Stulik, "Combined Atlantoaxial Fractures"; Acta Chir Orthop Traumatol Cech; 2005; pp. 105-110; vol. 72(2).

McGee, "A Simplified Galveston Technique for the Stabilization of Pathological Fractures of the Sacrum"; Eur. Spine J.; 2009; pp. 451-454; vol. 9.

Baldwin, "Sacral Fixation Using Iliac Instrumentation and a Variable-Angle Screw Device"; J. Neurosurg; 1994; pp. 313-316; vol. 81.

* cited by examiner

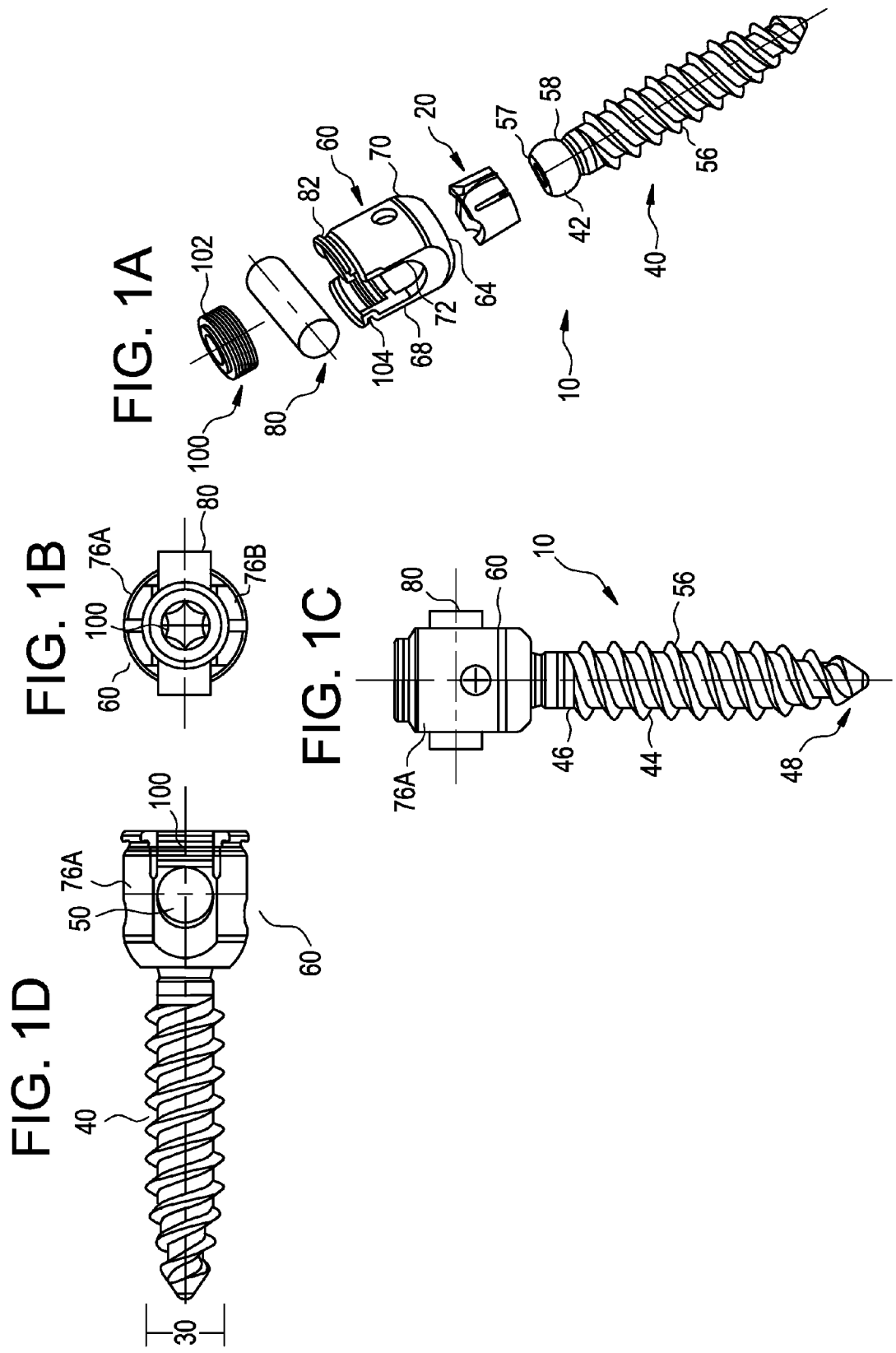

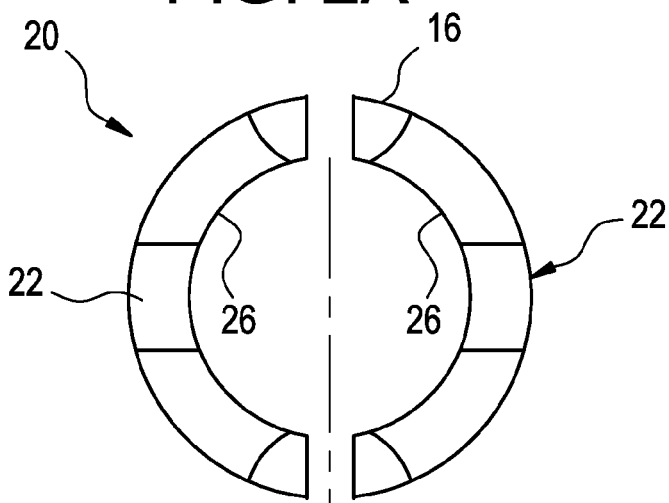
FIG. 2A
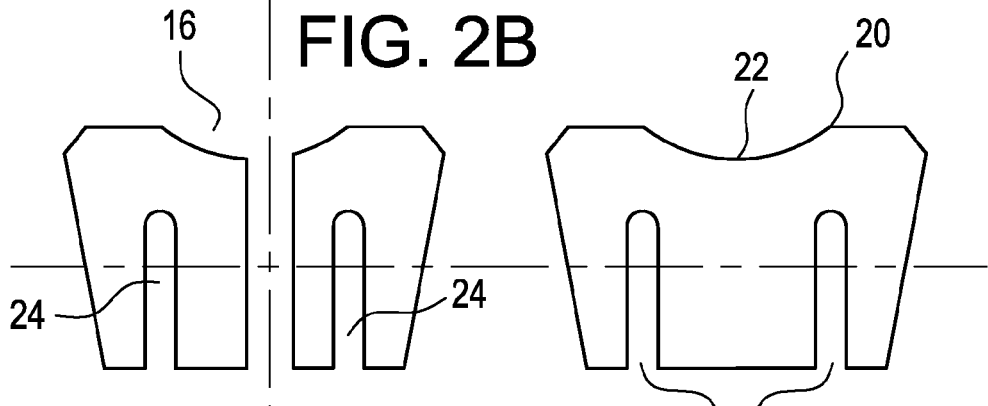
FIG. 2B
FIG. 2C
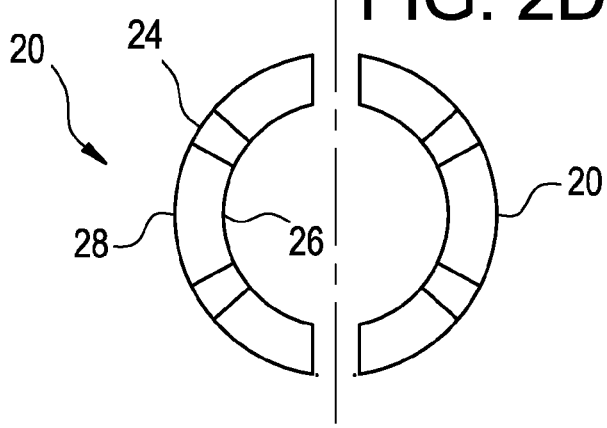
FIG. 2D

LARGE DIAMETER BONE ANCHOR ASSEMBLY

CONTINUING DATA

This application claims the benefit of U.S. Provisional Patent Application Ser. No. 60/796,019, entitled "Large Diameter Bone Anchor Assembly", filed Apr. 28, 2006, which is hereby incorporated by reference.

BACKGROUND

Spinal connection systems may be used in orthopedic surgery to align and/or fix a desired relationship between adjacent vertebrae. Such systems typically include a spinal connection element, such as a relatively rigid fixation rod or plate or a dynamic connector, that is coupled to adjacent vertebrae by attaching the element to various anchoring devices, such as hooks, bolts, wires, or screws. The spinal connection element can have a predetermined contour that has been designed according to the properties of the target implantation site, and once installed, the spinal connection element holds the vertebrae in a desired spatial relationship, either until desired healing or spinal fusion has taken place, or for some longer period of time.

Spinal connection elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal connection element receiving portion, which, in spinal rod applications, is usually in the form of a U-shaped slot formed in the head for receiving the rod. A set-screw, plug, cap or similar type of closure mechanism, may be used to lock the connection element into the connection element receiving portion of the pedicle screw. In use, the shank portion of each screw may be threaded into a vertebra, and once properly positioned, a connection element may be seated through the spinal connection element receiving portion of each screw and the connection element is locked in place by tightening a cap or similar type of closure mechanism to securely interconnect each screw and the connection element. Other anchoring devices also include hooks and other types of bone screws.

In certain procedures, such as those in the lumbar or sacral spine, it may be necessary to use a larger diameter pedicle screw capable of carrying large loads or engaging large pedicles. A difficulty in using a larger diameter screw comes from the corresponding increase in the size of the receiver head to accommodate the larger diameter screw shank, since the shank is usually assembled from the top through the opening at the proximal end of the receiver head. The increased size of the receiver head can interfere with the bony anatomy and can limit the polyaxial range of motion of the screw head. Another problem associated with manufacturing large diameter top-loading screws is that the opening in the receiver head has to be larger to accept the larger diameter screw shank, which creates the need for a larger closure mechanism. It is desirable to maintain the same size opening in the receiver head such that the same size closure mechanisms can be used. Accordingly, a larger diameter polyaxial screw is needed which is not top-loading.

SUMMARY

Disclosed herein are embodiments of a bottom-loading bone anchor assembly having a large diameter bone-engaging shank. In one embodiment, the bone anchor assembly includes a receiver member having an opening at the proximal end for receiving the connection element and a bore having a diameter greater than the opening; a bone-engaging shank having a head at a proximal end, the head sized to fit through the bore of the receiver member; and an insert having a slot extending through a portion of the insert, sized to fit within the receiver member wherein the insert retains the head of the shank within the receiver member. The assembly may further include a closure mechanism having a diameter smaller than the diameter of the head of the shank and/or the major diameter of the bone-engaging shank.

Also disclosed herein are methods of assembling a large diameter bone anchor assembly by positioning an insert having a slot extending from a distal end into a receiver member having an opening at a proximal end for receiving a spinal connection element and a bore at a distal end; inserting a bone-engaging shank having a head at a proximal end in a proximal direction through the bore of the receiver member; aligning the insert with the head of the bone-engaging shank; and swaging a side of the receiver member inward to retain the insert and the head of the shank.

BRIEF DESCRIPTION OF THE FIGURES

These and other features and advantages of the bone anchor assembly and methods disclosed herein will be more fully understood by reference to the following detailed description in conjunction with the attached drawings in which like reference numerals refer to like elements through the different views. The drawings illustrate principles of the bone anchor assembly and methods disclosed herein and, although not to scale, show relative dimensions.

FIG. 1A illustrates an exploded view of a large diameter bone anchor assembly.

FIG. 1B illustrates a top view of the bone anchor assembly shown in FIG. 1A.

FIG. 1C illustrates a side view of the bone anchor assembly shown in FIG. 1A.

FIG. 1D illustrates another side view of the bone anchor assembly shown in FIG. 1A.

FIG. 2A illustrates a top view of the inserts of the bone anchor assembly shown in FIG. 1A.

FIGS. 2B,2C illustrate side views of the inserts of the bone anchor assembly shown in FIG. 1A.

FIG. 2D illustrates a bottom view of the inserts of the bone anchor assembly shown in FIG. 1A.

DETAIL DESCRIPTION OF EXEMPLARY EMBODIMENTS

Figure 3A:
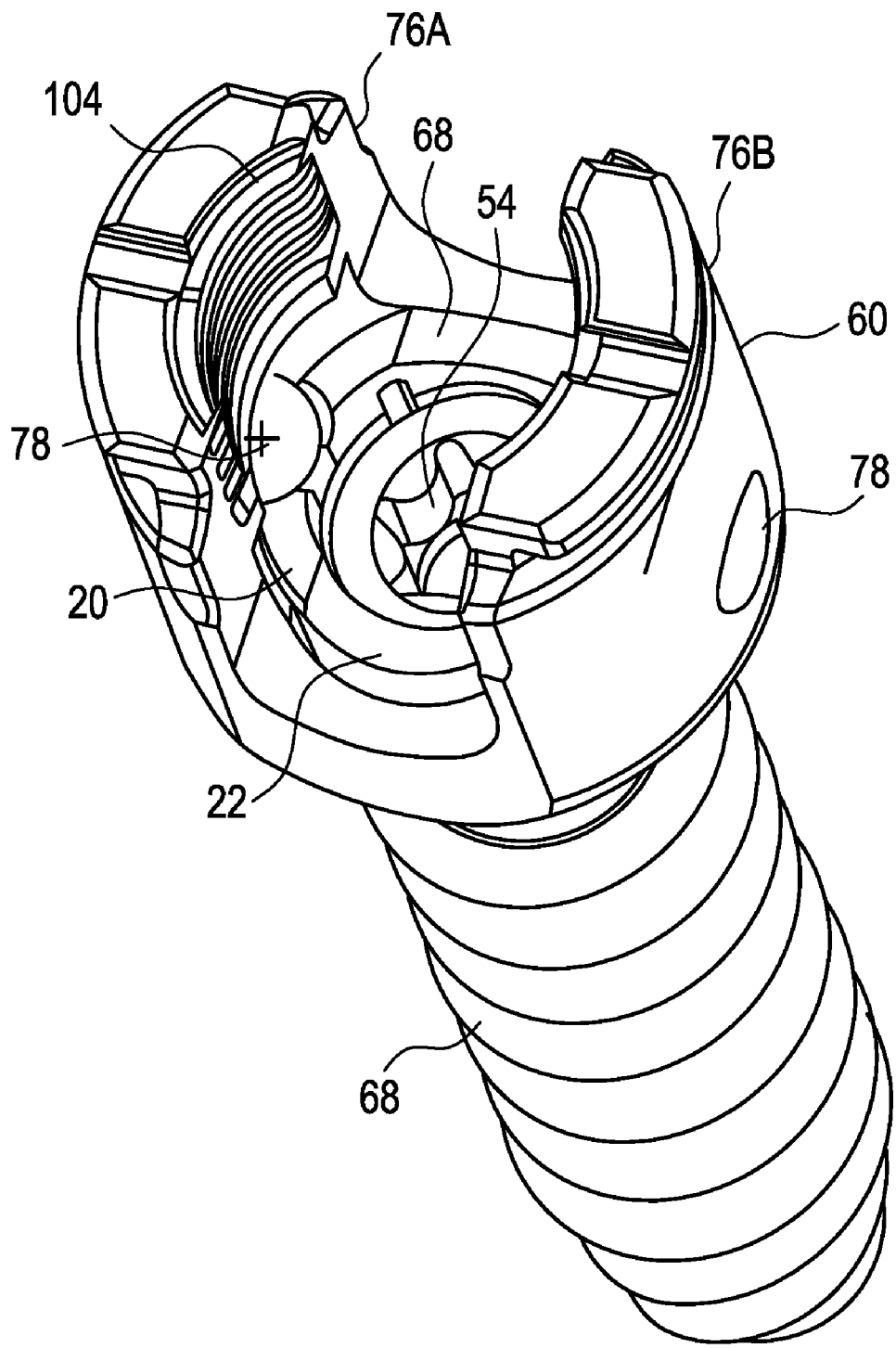
FIG. 3A illustrates a perspective view of the receiver member, inserts, and bone-engaging shank of the bone anchor assembly shown in FIG. 1A.
Figure 3B:
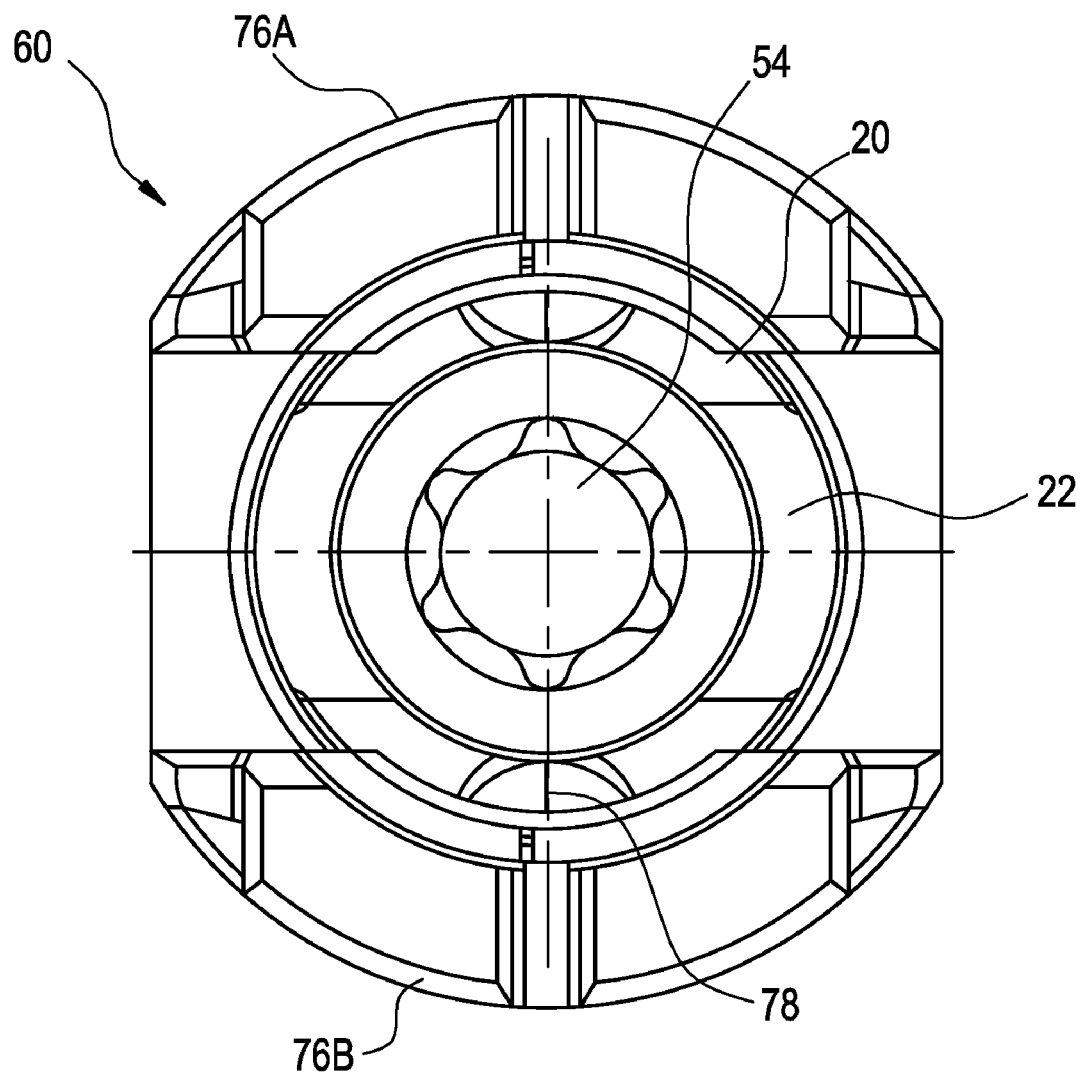
FIG. 3B illustrates a top view of the receiver member, inserts and bone-engaging shank of the bone anchor assembly shown in FIG. 3A.
Figure 3C:
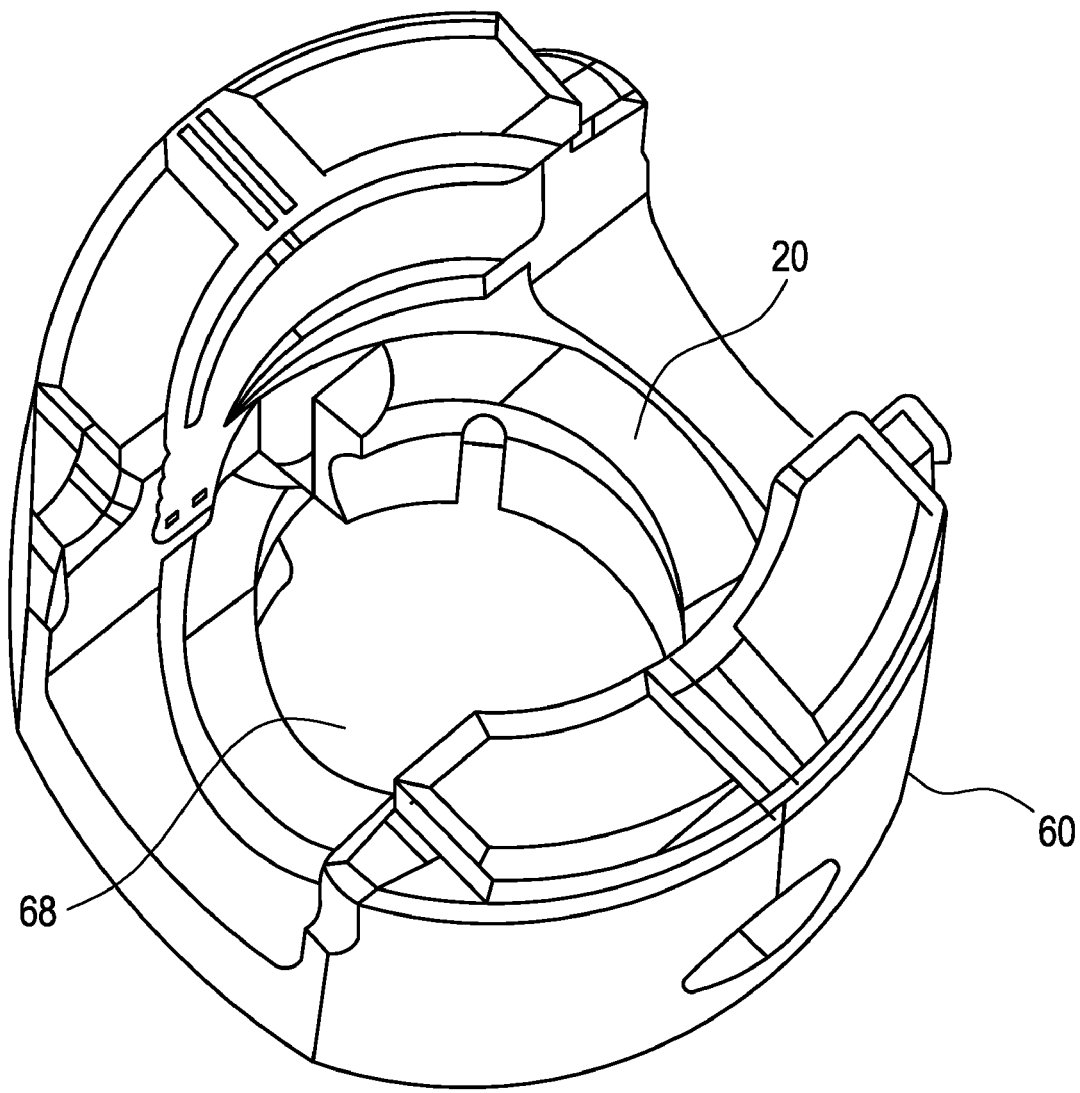
FIG. 3C illustrates a perspective view of the receiver member and inserts of the bone anchor assembly shown in FIG. 3A.

Certain exemplary embodiments will now be described to provide an overall understanding of the principles of the structure, function, manufacture, and use of the large diameter piece bone anchor assembly and methods disclosed herein. One or more examples of these embodiments are illustrated in the accompanying drawings. Those of ordinary skill in the art will understand that the large diameter bone anchor assembly and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-4 illustrate an exemplary embodiment of a bottom-loading large diameter bone anchor assembly. The exemplary bone anchor assembly 10 may be employed to engage one or more spinal connection elements to bone. For example, bone anchor assembly 10 may be employed to connect a spinal plate, rod (rigid or dynamic), and/or cable to a vertebra of the spine. Although the exemplary bone anchor assembly 10 described below is designed primarily for use in spinal applications, one skilled in the art will appreciate that the structure, features, and principles of the exemplary bone anchor assembly 10, as well as the other exemplary embodiments described below, may be employed to couple any type of orthopedic implant to any type of bone or tissue. Non-limiting examples of applications of the bone anchor assembly 10 described herein include long bone fracture fixation/stabilization, small bone stabilization, lumbar spine as well as thoracic stabilization/fusion, cervical spine compression/fixation, dynamic, non-fusion applications including facet replacement and dynamic posterior systems as well as skull fracture/reconstruction plating.

The illustrated exemplary bone anchor assembly 10 shown in FIGS. 1A-D includes a bone-engaging shank 40 configured for engaging bone, a receiver member 60 for receiving a spinal connection element, and an insert 20 for retaining the shank 40 within the receiver member 60. The bone-engaging shank 40 extends from a proximal end 46 to a distal end 48 along a longitudinal axis. An outer surface 44 of the bone-engaging shank 40 extends between the proximal end 46 and the distal end 48. The outer surface 44 of the bone-engaging shank 40 may include one or more bone engagement mechanisms to facilitate gripping engagement of the bone anchor assembly 10 to bone. In the illustrated exemplary embodiment, for example, the bone-engaging shank 40 includes an external thread 56. The external thread 56 may extend along at least a portion of the bone-engaging shank 40. For example, in the illustrated exemplary embodiment, the external thread 56 extends from the distal end 48 to the proximal end 46 of the bone-engaging shank 40. One skilled in the art will appreciate that bone engagement mechanisms other than external thread 56 may be employed, including, for example, one or more annular ridges, multiple threads, dual lead threads, variable pitched threads, and/or any other conventional bone engagement mechanism. In the illustrated exemplary embodiment, the shank diameter 30 of bone-engaging shank 40 may be defined by the major diameter of external thread 56.

The proximal end 46 of the exemplary bone-engaging shank 40 has a head 42 configured to fit within the receiver member 60 and to facilitate adjustment of the shank 40 relative to the receiver member 60. For example, the head 42 may be generally spherical in shape to permit pivoting of the bone-engaging shank 40 relative to the receiver member 60. In the illustrated exemplary embodiment, for example, the head 42 may be in the shape of a truncated sphere having a generally planar proximal surface 57 and a generally hemispherically shaped distal surface 58. The head 42 of the shank 40 may have surface texturing, knurling, and/or ridges. A drive feature 54 may be located internally or externally on the head 42 of the shank 40.

Figure 4A:
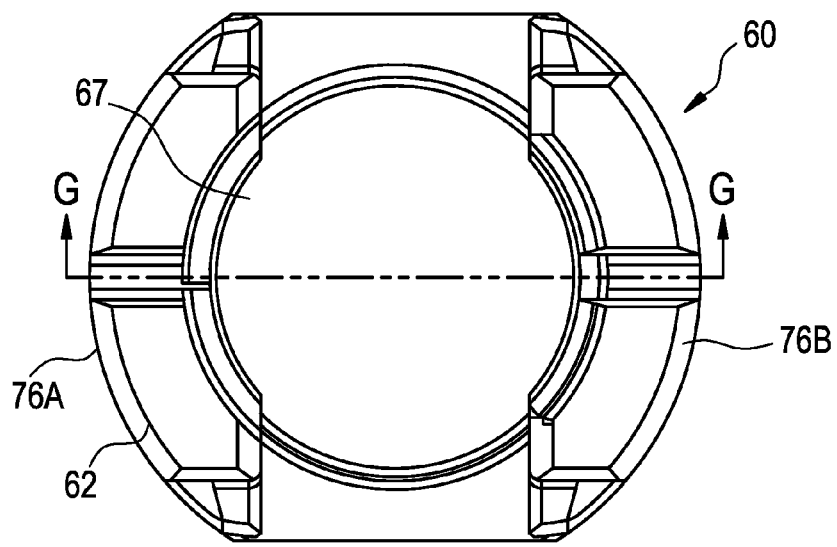
FIG. 4A shows a top view of the receiver member of the bone anchor assembly shown in FIG. 1A.
Figure 4B:
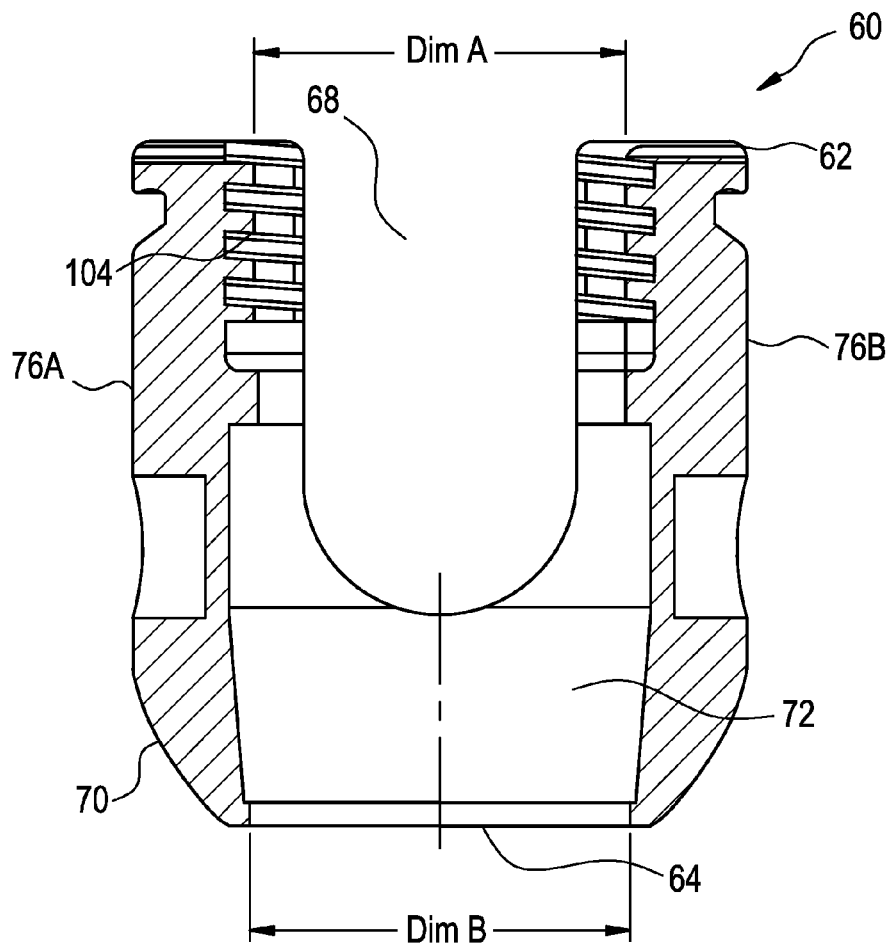
FIG. 4B shows a cross-section of the receiver member shown in FIG. 4A.

Referring to FIGS. 4A-B, the receiver member 60 of the exemplary bone anchor assembly 10 includes a proximal end 62 having a cylindrical opening leading to recess 68, and a distal end 70 having a bore 64 forming a seat portion 72. The receiver member 60, in certain exemplary embodiments, may be configured to receive a spinal connection element and couple the spinal connection element to the bone anchor assembly. In the exemplary embodiment, for example, the recess 68 of the receiver member 60 may be sized and shaped to receive a spinal rod 80, as illustrated in FIG. 1A. For example, the receiver member 60 has a generally U-shaped cross-section defined by two legs 76A and 76B separated by recess 68. Each leg 76A, 76B is free at the proximal end 62 of the receiver member 60. In the exemplary embodiment, for example, the inner surfaces 104 of the legs 76A, 76B are threaded to mate with a corresponding thread on the closure mechanism shown as a setscrew 100. The exemplary spinal rod 80 may be seated within the recess 68 by aligning the spinal rod 80 and the recess 68 and advancing the spinal rod 80 between the legs 76A, 76B into the recess 68. The configuration of recess 68 of the receiver member 60 may be varied to accommodate the type, size and shape of spinal connection element employed.

In the exemplary embodiment, the bore 64 of the receiver member 60 is sized to receive at least a portion of a bone anchor assembly, such as the head 42 of the shank 40. For example, the head 42 of the shank 40 may be inserted in the proximal direction through the bore 64 of the receiver member 60, as illustrated in FIG. 1A. In the exemplary embodiment, the diameter of the bore 64 may be greater than the diameter of the opening 67 of the receiver member 60 at the proximal end 62. In the exemplary embodiment, the major diameter 30 of the shank 40 may be greater than the diameter of the closure mechanism 100 and the opening 67 of the receiver member 60. In other exemplary embodiments, the diameter of the bore 64 may be equal to or less than the diameter of the opening 67 and the major diameter 30 may be less than or equal to the diameter of the closure mechanism 100 and the opening 67 of the receiver member 60.

The distal end 70 of the receiver member 60 may be sized and shaped to accommodate the head 42 of the shank 40. For example, the distal end 70 may define a seat portion 72 for accommodating the head 42 of the shank 40 allowing the bone-engaging shank 40 to pivot relative to the receiver member 60. In some exemplary embodiments, the seat portion 72 may be generally spherical in shape to permit pivoting of the bone-engaging shank 40 relative to the receiver member 60. In the illustrated exemplary embodiment, the seat portion 72 may be generally hemispherical in shape and may have a curvature analogous to the distal surface 58 of the head 42 of the core shank 40. In other exemplary embodiments, the seat portion 72 may be tapered or may have any other shape that allows adjustment of the head 42 of the shank 40 relative to the receiver member 60. In the exemplary embodiment, the bone anchor assembly 10 is a polyaxial bone anchor assembly. The bone-engaging shank 40 when assembled with the insert 20 within the receiver member 60 may be pivoted to one or more angles relative to the receiver member 60.

Referring to FIG. 1A, first and second inserts 20 of the bone anchor assembly 10 are positionable between the inner surface of the receiver member 60 and the outer surface of the head 42 of the shank 40. The inserts 20 are positioned about the head 42 and cooperate to retain the head 42 of the shank 40 within the receiver member 60. In the exemplary embodiment shown in FIGS. 2A-D, the first and second inserts 20 may have a proximal surface 22 shaped for engaging the spinal rod or a spinal connection element. The insert 20 may have an inner surface 26 contoured with a semi-spherical shape for engaging the head 42 of the shank 40 and an outer surface 28 having a semi-circular shape and tapered for engaging a portion of the seat 72 of the receiver member 60. The inner surface 26 of the insert 20 may be textured for better gripping of the head 42 of the shank 40. Examples of texturing include knurling, blasting, or ridges. The insert 20 extends from a proximal end 12 to a distal end 14. In the exemplary embodiment, the insert 20 may taper from the proximal end 12 to the distal end 14. A slot 24 extends proximally from the distal end 14 of the insert providing flexibility to the insert. The proximal corners 16 of the insert may be contoured. The insert 20 has a generally semi-circular shape when viewed from the top as shown in FIG. 2A. One skilled in the art will recognize that any number of inserts 20 may be used in the bone anchor assembly to retain the head 43 of the shank 40 within the receiver member 60.

The exemplary bone anchor assembly 10 may include a closure mechanism 100 that secures the spinal connection element to the bone anchor assembly. Referring to FIGS. 1A-D, the closure mechanism 100 secures the exemplary spinal rod 80 within the recess 68 of the receiver member 60. The closure mechanism 100 may engage the proximal end 62 of the receiver member 60 or, in other exemplary embodiments, may engage other portion(s) of the receiver member 60. The exemplary closure mechanism 100 is an internal setscrew that engages an inner surface of the proximal end 62 of the receiver member 60. For example, the closure mechanism 100 may have external threads 102 that engage internal threads 104 provided on the proximal end 62 of the receiver member 60. Distal advancement of the closure mechanism 100 into engagement of the spinal rod 80, seats the spinal rod 80 in the proximal surface 22 of the insert 20. The insert 20 then is advanced into the seat portion 72 of the receiver member 60 causing the insert 20 to move distally against the inner surface of the receiver member and compress or flex inwardly against the head 42 of the shank 40 thereby fixing the relative movement of the head 42 in relation to the receiver member 60. In one embodiment, the major diameter 30 of the bone-engaging shank 40 may be greater than the diameter of the closure mechanism 100 and the opening 67 of the receiver member 60.

One skilled in the art will appreciate that other types of closure mechanisms may be employed. For example, an external closure mechanism positionable around the outer surface of the legs 76A, 76B of the receiving member 60 may be employed. In other exemplary embodiments, the closure mechanism may comprise an external and an internal closure mechanism, a non-threaded twist-in cap, and/or any other conventional closure mechanism.

The components of the bone anchor assembly may be manufactured from any biocompatible material, including, for example, metals and metal alloys such as titanium and stainless steel, polymers, and/or ceramics. The components may be manufactured of the same or different materials. In one exemplary method of manufacturing, the bone-engaging shank 40, the insert 20 and the receiver member 60 are separately constructed and assembled prior to implantation. The first and second inserts 20 in one exemplary method may be inserted within the receiver member 60 either through the bore 64 at the distal end or the opening 67 at the proximal end 62 extending into the recess 68. The shank 40 may be coupled to the receiver member 60 by positioning the head 42 of the shank 40 through the bore 64 at the distal end 70 of the receiver member 60. The inserts 20 are advanced into the receiver member 60 until the head 42 of the shank 40 expands the slot 24 of the insert 20 around the head 42 seating the head 42 against inner surface of the insert 20 such that the distal end 48 of the shank 40 extends through the bore 64. While maintaining the alignment of the insert 20 and the head 42 of the shank 40, the outer side surfaces of the receiver member 60 may be swaged inwardly to retain the insert 20 in place with the head 42 of the shank 40 within the receiver member 60. The swaged protrusion 78 extends between the contoured corners 28 of the insert 20 to prevent the insert 20 from moving in the proximal direction.

While the large diameter bone anchor assembly and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A bone anchor assembly for engagement to a connection element comprising:
   a receiver member having a proximal opening at the proximal end for receiving the connection element and a bore at the distal end, the bore terminating at a distal opening having a diameter greater than the proximal opening;
   a bone-engaging shank having a head at a proximal end, the head sized to fit through the distal opening of the bore of the receiver member;
   a semi-spherical shaped first insert;
   a semi-spherical shaped second insert separate and unconnected to the first insert, the first insert and the second insert each sized to fit within the receiver member, the first insert and the second insert each having a proximal end shaped for engaging the connection element and an inner surface shaped to engage the head of the bone shank, the first insert and the second insert positioned about the head; and
   a closure mechanism for securing the connection element to the bone anchor assembly, wherein distal advancement of the closure mechanism seats the connection element against the proximal end of the first insert and the proximal end of the second insert and seats the head of the bone shank against the inner surface of the first insert and the inner surface of second insert, the first insert and the second insert cooperating to retain the head of the shank within the receiver member.

2. The bone anchor assembly of claim 1, wherein the head of the shank has a generally spherical shape.

3. The bone anchor assembly of claim 1, wherein the first and second inserts have contoured corners.

4. The bone anchor assembly of claim 1, wherein the first and second inserts have a textured surface for engaging the head of the shank.

5. The bone anchor assembly of claim 1, wherein the first and second inserts have a slot extending through a portion thereof for providing flexibility to the inserts.

6. The bone anchor assembly of claim 1, wherein the shank has a major diameter that is greater than the diameter of the closure mechanism.

7. The bone anchor assembly of claim 1, wherein the shank has a major diameter that is greater than the diameter of the proximal opening of the receiver member.

8. The bone anchor assembly of claim 1, wherein the first insert and the second insert are sized to fit through the proximal opening of the receiver member.

9. The bone anchor assembly of claim 1, wherein the first insert and the second insert are retained within the receiver member by swage protrusions.

10. A method of assembling a large diameter bone anchor assembly comprising:

positioning a semi-spherically shaped first insert having a slot extending from a distal end into a receiver member having a proximal opening at a proximal end for receiving a spinal connection element and a bore at a distal end, the bore terminating at a distal opening;

positioning a semi-spherically shaped second insert having a slot extending from a distal end into the receiver member, the second insert being separate and unconnected to the first insert;

inserting a proximal head of a bone-engaging shank in a proximal direction through the distal opening of the bore of the receiver member;

positioning the first and second inserts about the head of the bone-engaging shank; and swaging a side of the receiver member inward to retain the inserts and the shank.

11. The method of claim 10, wherein the insert is positioned into the opening of the receiver member at the proximal end.

\* \* \* \* \*